(12) United States Patent
Yang et al.

(10) Patent No.: US 12,133,730 B2
(45) Date of Patent: Nov. 5, 2024

(54) SYSTEMS AND METHODS FOR EVALUATING MINDFULNESS

(71) Applicant: Qatar Foundation for Education, Science and Community Development, Doha (QA)

(72) Inventors: David Yang, Doha (QA); Anis Troudi, Doha (QA); Dena Al Thani, Doha (QA); Amine Bermak, Doha (QA); Mounir Hamdi, Doha (QA)

(73) Assignee: QATAR FOUNDATION FOR EDUCATION, SCIENCE AND COMMUNITY DEVELOPMENT, Doha (QA)

( * ) Notice: Subject to any disclaimer, the term of this patent is extended or adjusted under 35 U.S.C. 154(b) by 456 days.

(21) Appl. No.: 17/559,015

(22) Filed: Dec. 22, 2021

(65) Prior Publication Data

US 2022/0192560 A1    Jun. 23, 2022

Related U.S. Application Data

(60) Provisional application No. 63/130,001, filed on Dec. 23, 2020.

(51) Int. Cl.
*G06N 3/00* (2023.01)
*A61B 5/00* (2006.01)
(Continued)

(52) U.S. Cl.
CPC .............. *A61B 5/165* (2013.01); *A61B 5/004* (2013.01); *A61B 5/163* (2017.08); *A61B 5/168* (2013.01); *G06N 3/02* (2013.01); *G16H 20/70* (2018.01)

(58) Field of Classification Search
CPC ......... A61B 5/165; A61B 5/004; A61B 5/163; A61B 5/168; A61B 5/0077; G06N 3/02;
(Continued)

(56) References Cited

U.S. PATENT DOCUMENTS

| 10,347,072 B2 | 7/2019 | Froy et al. |
| 10,365,716 B2 | 7/2019 | Aimone et al. |

(Continued)

OTHER PUBLICATIONS

Al-Rahayfeh, et al.; "Eye Tracking and Head Movement Detection: A State-of-Art Survey"; Rehabilitation Devices and Systems; Nov. 2013; (12 pages).

(Continued)

*Primary Examiner* — Van D Huynh
(74) *Attorney, Agent, or Firm* — K&L Gates LLP

(57) ABSTRACT

The present application provides an AI-based system for evaluating an individual's mindfulness (e.g., during prayer) based on video captured of the individual. In one example, the video may be captured via a smart phone. The individual's mindfulness may be continually evaluated from the captured video by observing the individual's body pose and movements. For instance, turning the individual's head to one side or moving the individual's eyes around rapidly can be signs of losing focus. Body pose and movement information of an individual may be derived from the video through AI-based video analytics. The user's body pose and movements may be checked against a set of predefined criteria for mindfulness, and an objective evaluation may be provided. Such evaluation can then be fed back to the individual, for example, to remind the individual whenever they lose focus during prayer.

19 Claims, 4 Drawing Sheets

(51) Int. Cl.
*A61B 5/16* (2006.01)
*G06N 3/02* (2006.01)
*G16H 20/70* (2018.01)

(58) Field of Classification Search
CPC ........ G06N 20/00; G16H 20/70; G16H 50/30;
G16H 50/20
See application file for complete search history.

(56) References Cited

U.S. PATENT DOCUMENTS

| | | | |
|---|---|---|---|
| 2013/0069773 A1* | 3/2013 | Li | B60W 30/0956 340/436 |
| 2014/0184797 A1* | 7/2014 | Ko | H04N 7/18 348/148 |
| 2015/0351655 A1 | 12/2015 | Coleman | |
| 2017/0039045 A1 | 2/2017 | Abrahami et al. | |
| 2021/0188288 A1* | 6/2021 | Yagi | B60W 10/30 |
| 2021/0240968 A1* | 8/2021 | Kei | G06V 40/161 |
| 2021/0290102 A1* | 9/2021 | Burwinkel | G16H 50/20 |

OTHER PUBLICATIONS

Smith, et al; "Monitoring Head/Eye Motion for Driver Alertness with One Camera"; Computer Science, University of Central Florida; (7 pages).
Chang, et al; "Using Eye Tracking to Assess Gaze Concentration in Meditation"; MDPI; Apr. 2019; (14 pages).

* cited by examiner

SYSTEMS AND METHODS FOR EVALUATING MINDFULNESS

PRIORITY CLAIM

The present application claims priority to and the benefit of U.S. Provisional Application 63/130,001, filed Dec. 23, 2020, the entirety of which is herein incorporated by reference.

BACKGROUND

Maintaining one's attention is an important skill for a variety of activities. This can also be termed as mindfulness or staying in the present moment. In one example, maintaining one's attention in the present moment is an important aspect of Islamic prayer. Holding one's attention for an extended period of time, however, can be challenging due to distractions, mental fatigue, or other factors. For instance, it can be particularly challenging for children or new Muslims to hold their attention for an extended period during Islamic prayer.

In some instances, individuals may try to increase their mindfulness or attention by creating an environment conducive for maintaining their mindfulness or attention. For example, Islamic practitioners may use a special prayer room, burn incense, or perform ablution. Even with these environmental factors, however, an individuals' attentions can gradually drift away.

To help alert an individual when the individual's attention has drifted, various systems exist that capture the individual's movements, such as with a camera, to determine whether the individual's movements are consistent with the individual being mindful. For example, these typical systems may track an individual's eye or head movement. If the movements are not consistent, the system may alert the individual that the individual's attention has drifted. Some of these systems may utilize machine learning to determine whether the individual's movements are consistent with mindfulness. Upon being alerted, the individual may refocus their attention. The individual may also utilize the system as a training tool to help train the individual's mindfulness capability so that the individual is alerted less often.

These typical systems for tracking an individual's attention focus or mindfulness, however, are not always accurate. If a system alerts an individual that they have lost focus, when the individual had not in fact lost focus, then the system itself makes the individual lose focus. Such typical systems can therefore be counterproductive if they generate too many errors. Conversely, if such a system fails to alert an individual when the individual has lost focus, then the system does not serve its purpose. Accordingly, a system that improves upon the accuracy of typical systems for tracking an individual's attention or mindfulness is desired.

SUMMARY

The present application provides a system for evaluating an individual's mindfulness based on captured video of the individual. From the captured video, the provided system may use a machine learning model to extract various features of the individual, such as the individual's eye and head movements and whether the individual is smiling. Using the extracted features, the system determines whether the individual is being mindful. The system may alert an individual if it is determined that the individual is not being mindful in order to gather the individual's attention back.

In an example, a system for detecting whether an individual's attention is maintained includes a camera configured to capture video, a memory, and a processor in communication with the memory. The system captures video of the individual via the camera. The system uses at least one first model to extract a plurality of features of the individual from the captured video. The plurality of features include a plurality of positions of a left eye of the individual, a plurality of positions of a right eye of the individual, a plurality of roll angles of the individual's head, a plurality of yaw angles of the individual's head, a probability that the individual is smiling, a probability that the left eye is closed, and a probability that the right eye is closed. The system determines, via at least one second model, whether the individual's attention is maintained based on the plurality of extracted features and a plurality of weighting factors. The system may cause an alert to be generated in response to determining that the individual's attention is not maintained.

In another example, a method for detecting whether an individual's attention is maintained includes capturing video of the individual via a camera. A plurality of features of the individual are extracted, via at least one first model, from the captured video. The plurality of features include a plurality of positions of a left eye of the individual, a plurality of positions of a right eye of the individual, a plurality of roll angles of the individual's head, a plurality of yaw angles of the individual's head, a probability that the individual is smiling, a probability that the left eye is closed, and a probability that the right eye is closed. It is determined, via at least one second model, whether the individual's attention is maintained based on the plurality of extracted features and a plurality of weighting factors. An alert is generated in response to determining that the individual's attention is not maintained.

In another example, a non-transitory, computer-readable medium storing instructions is provided, which when the instructions are executed by a processor, the instructions cause the processor to capture, via a camera, video of an individual. The instructions further cause a plurality of features of the individual to be extracted, via at least one first model, from the captured video. The plurality of features include a plurality of positions of a left eye of the individual, a plurality of positions of a right eye of the individual, a plurality of roll angles of the individual's head, a plurality of yaw angles of the individual's head, a probability that the individual is smiling, a probability that the left eye is closed, and a probability that the right eye is closed. The instructions further cause the processor to determine, via at least one second model, whether the individual's attention is maintained based on the plurality of extracted features and a plurality of weighting factors. The instructions may cause an alert to be generated in response to determining that the individual's attention is not maintained.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

The present application provides an AI-based system for evaluating an individual's mindfulness (e.g., during prayer) based on video captured of the individual. In one example, the video may be captured via a smart phone. The smart phone may capture video of an individual and evaluate the individual's mindfulness by extracting the individual's body pose and movements from the captured video using a machine-learning model. For instance, turning the individual's head to one side or moving the individual's eyes around rapidly can be signs of losing focus. The smart phone may check the user's extracted body pose and movements against a set of predefined criteria for mindfulness, and provide an objective evaluation. Such evaluation can then be fed back to the individual in the form of an alert.

Figure 1:
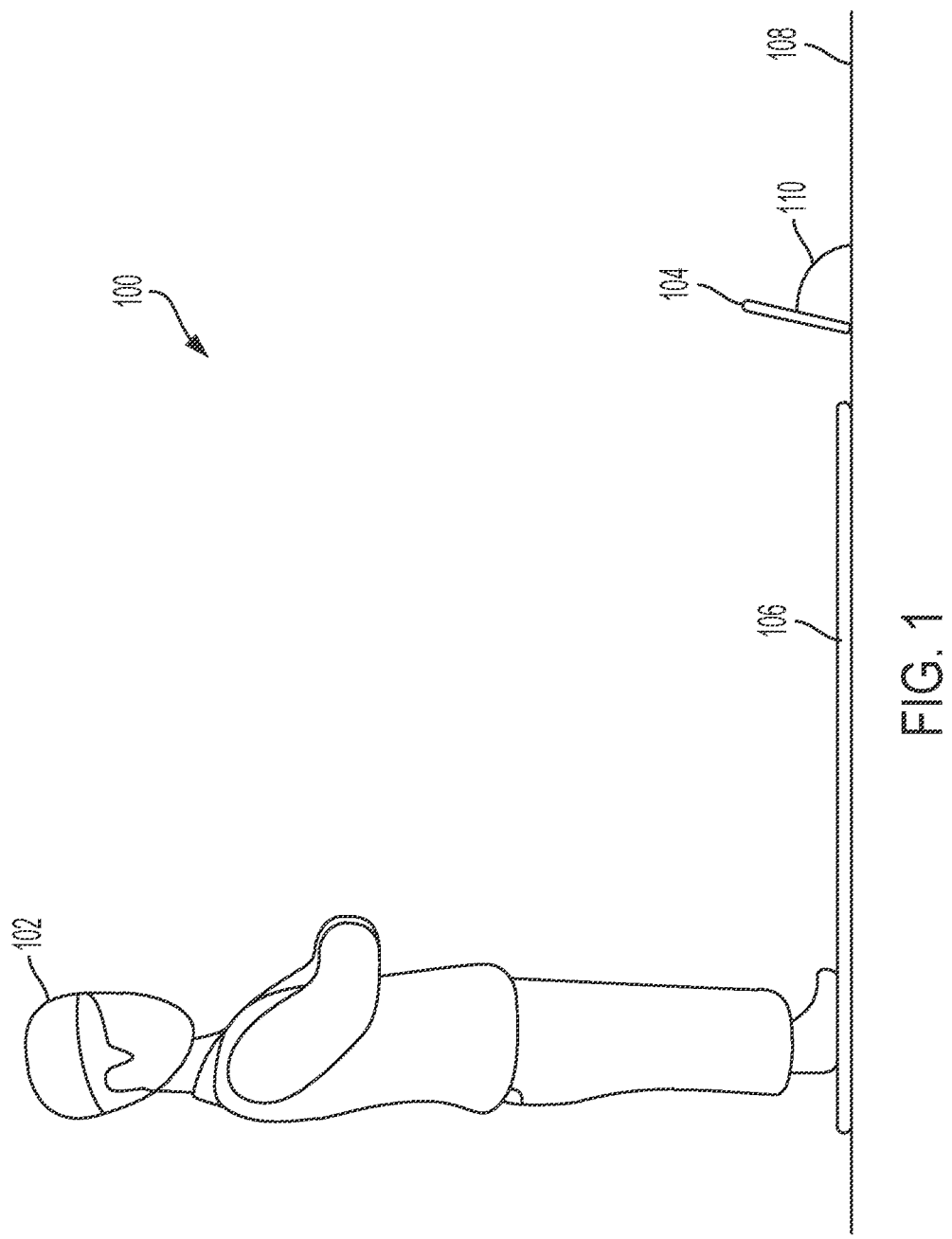
FIG. 1 illustrates an example system for detecting whether an individual is being mindful using a mindfulness detection system, according to an aspect of the present disclosure.

Individuals may use the provided system to alert themselves that they are no longer being mindful during any suitable activity. For example, FIG. 1 illustrates an example system 100 for detecting whether an individual 102 is being mindful during a prayer using a mindfulness detection system 104. In the example, the individual 102 is standing, though in other examples the individual may be sitting in a chair, sitting on the ground, kneeling, etc. The individual is shown standing on a mat 106, such as an Islamic prayer mat, placed on the ground 108. In other examples, the individual may be standing on the ground 108 or another other suitable surface.

The mindfulness detection system 104 is positioned such that a camera 206 (FIG. 2) of the mindfulness detection system 104 is aimed at the individual to capture the individual's movements. The mindfulness detection system 104 may be a smartphone, tablet, laptop, or other suitable mobile computing device. For instance, an application installed on a smartphone or tablet may execute the mindfulness detection method described herein. In one example, the mindfulness detection system 104 may include a computing device and a separate camera 206 in communication (e.g., wireless) with the computing device. In various aspects, the mindfulness detection system 104 may be maintained at a particular angle 110 relative to the ground 108, or relative to the individual 102, to help the camera 206 of the mindfulness detection system 104 capture the features of the individual 102 needed for mindfulness detection. For example, the mindfulness detection system 104 may be maintained at an angle 110 of 45° from the ground 108. In some aspects, the system 100 may include a stand (not shown) that helps maintain the mindfulness detection system 104 at this particular angle 110.

In some aspects, the mindfulness detection system 104 may communicate over a network (not shown) with a server (not shown) or other suitable computing device. For example, the server may store a machine learning model and/or data used to train the machine learning model. In such aspects, the network can include, for example, the Internet or some other data network, including, but not limited to, any suitable wide area network or local area network. In other aspects, the mindfulness detection system 104 may have the requisite computing power and store the requisite data in order to make mindfulness determinations entirely contained within the mindfulness detection system 104. Stated differently, in such other aspects, the mindfulness detection system 104 does not communicate with an external server or any other system. In some examples, the mindfulness detection system 104 may communicate with a suitable device (e.g., a smartwatch) over a short-range communication protocol such as Bluetooth™, WiFi™, Zigbee®, Z-Wave®, wireless Universal Serial Bus ("USB"), or infrared protocols, or via any other suitable wireless communication technology. For example, the mindfulness detection system 104 may transmit a command to a smartwatch worn by the individual 102 for the smartwatch to vibrate when the mindfulness detection system 104 detects that the individual 102 is not being mindful.

Figure 2:
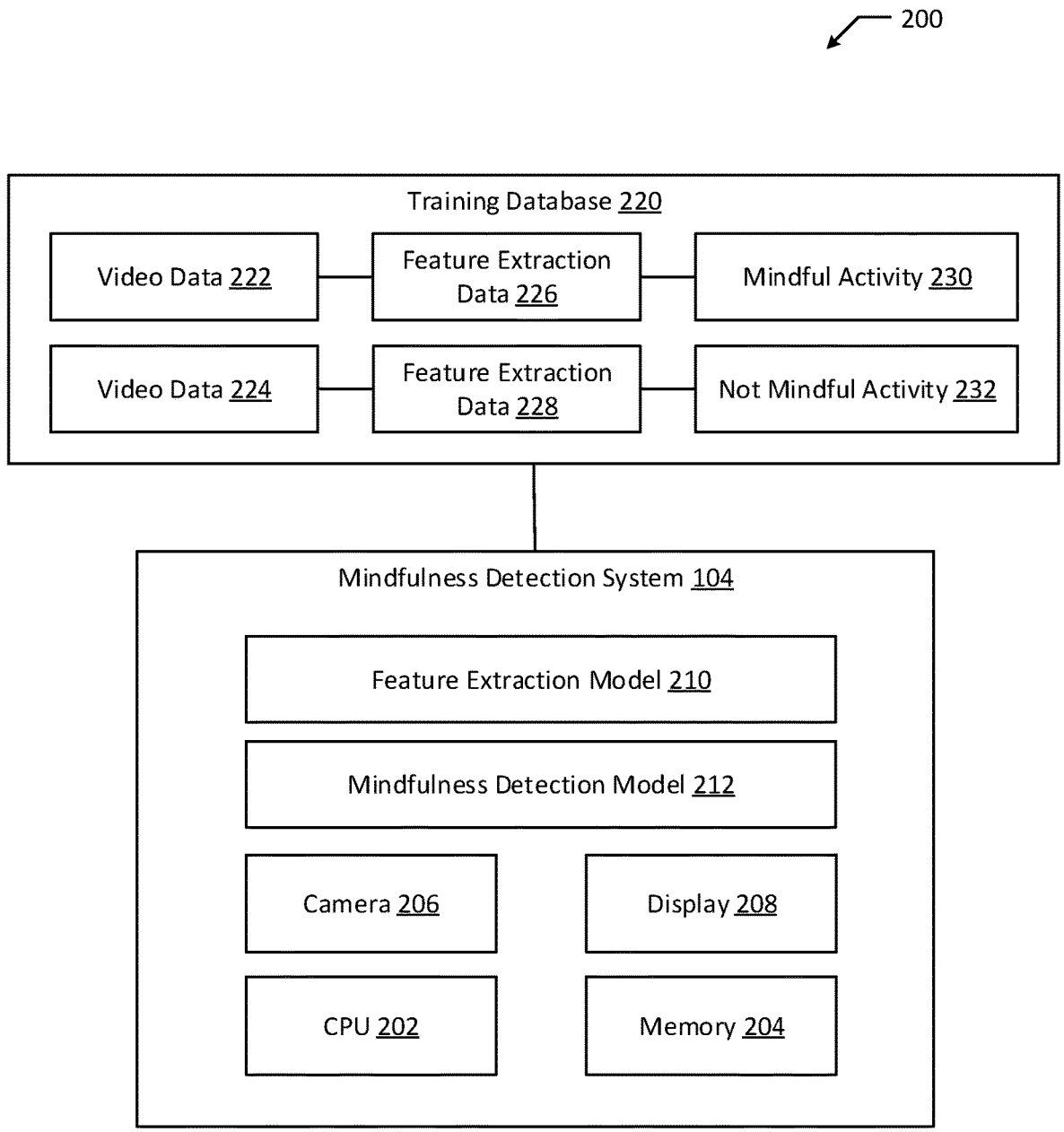
FIG. 2 illustrates a box diagram of mindfulness detection system of FIG. 1, according to an aspect of the present disclosure.

The mindfulness detection system 104 includes one or more models for determining whether the individual 102 is being mindful. FIG. 2 illustrates a box diagram of an example system 200 for training the model(s) of the mindfulness detection system 104. The system 200 includes the mindfulness detection system 104 and a training database 220. The mindfulness detection system 104 includes a processor in communication with a memory 204. The processor may be a CPU 202, an ASIC, or any other similar device. The mindfulness detection system 104 may include a camera 206 that is capable of capturing video. In some aspects, the mindfulness detection system 104 may include a display 208. The display 208 may be any suitable display for presenting information to the individual 102 such as the typical smartphone display. In other examples, the components of the mindfulness detection system 104 and/or the system 200 may be combined, rearranged, removed, or provided on a separate device or server.

In at least some aspects, the mindfulness detection system 104 may include one or more feature extraction models 210 trained to extract features (e.g., eye and head movement) of an individual from a video. The one or more feature extraction models 210 may be implemented by one or more suitable machine learning models, including one or more supervised learning models, unsupervised learning models, or other types of machine learning models. For example, the one or more feature extraction models 210 may be implemented as one or more of a neural network (e.g., neural networks with dense mapping, convolutional neural networks, or recurrent neural networks). In one particular example, the one or more feature extraction models 210 is a convolutional neural network.

In some aspects, the mindfulness detection system 104 may include one or more mindfulness detection models 212 trained to determine whether an individual is mindful from the features extracted by the feature extraction model 210. In some instances, the one or more feature extraction models 210 may be a subcomponent of the one or more mindfulness detection models 212. Stated differently, the one or more feature extraction models 210 may be used to extract features for the one or more mindfulness detection models of the mindfulness detection system 104 rather than features being manually determined. The one or more mindfulness detection models 212 may be implemented by one or more suitable machine learning models, including one or more supervised learning models, unsupervised learning models, or other types of machine learning models. For example, the one or more mindfulness detection models 212 may be implemented as one or more of a neural network (e.g., neural networks with dense mapping, convolutional neural networks, or recurrent neural networks), a decision tree model, a support vector machine, and a Bayesian network. In one particular example, the one or more mindfulness detection models 212 is at least one neural network model that outputs probabilities that an individual is not being mindful. If the output probability is greater than a predetermined threshold (e.g., 50%), then it is determined that the individual is not being mindful. The predetermined threshold can be adjusted to adjust the sensitivity of the mindfulness detection system 104. In some aspects, a difference between class probabilities may be taken as a confidence score, in which larger differences mean a more confident neural network model, and the confidence score can be used to set the predetermined threshold.

In at least some examples, the one or more machine learning models implementing the one or more feature extraction models 210 and the one or more mindfulness detection models 212 may be trained on video data captured by users of the mindfulness detection system 104. For instance, the one or more feature extraction models 210 and the one or more mindfulness detection models 212 may be trained based on video data including an individual being mindful and video data including a distracted individual (e.g., not being mindful). As a specific example, the system 200 includes the training database 220, which may store data used to train the one or more feature extraction models 210 and the one or more mindfulness detection models 212. In particular, the training database 220 stores video data 222, 224 in association with feature extraction data 226, 228, which is in association with identifiers of mindful activity 230 or not mindful activity 232. The video data 222, 224 may also be in association with the identifiers of mindful activity 230 or not mindful activity 232. The video data 222, 224 may include multiple frames. In one example, each frame of the video data 222, 224 may be in association with the identifiers of mindful activity 230 or not mindful activity 232.

To train the one or more feature extraction models 210, the mindfulness detection system 104 may analyze one or more sets of video data 222, 224 with the one or more feature extraction models 210 to generate the feature extraction data 226, 228. A set of feature extraction data 226, 228 may include a set of multiple features for a single feature. The features extracted by the one or more feature extraction models 210 may be analyzed to determine the accuracy of the one or more feature extraction models 210. For example, domain experts may analyze the feature extraction data 226, 228 to determine whether the one or more feature extraction models 210 correctly extracted eye and head movement features from the video data 222, 224. Parameters of the one or more feature extraction models 210 may be updated based on the accuracy of the output of the one or more feature extraction models 210.

To train the one or more mindfulness detection models 212, the mindfulness detection system 104 may analyze one or more sets of features extracted by the one or more feature extraction models 212 with the one or more mindfulness detection models 212 to detect whether an individual is being mindful. The detections by the one or more mindfulness detection models 212 may be compared to the identifier of mindful activity 230 or not mindful activity 232 associated with each set of video data 222, 224 and/or each set of feature extraction data 226, 228. Parameters of the one or more mindfulness detection models 212 may be updated based on whether the one or more mindfulness detection models 212 correctly detect whether the video data 222, 224 and/or the feature extraction data 226, 228 is associated with an identifier of mindful activity 230 or not mindful activity 232. One or more of the one or more mindfulness detection models 212 may include weights (e.g., priorities) for different features and combinations of features of extracted feature data 226, 228. Updating the parameters of the one or more mindfulness detection models 212 may include updating one or more of the features extracted by the one or more feature extraction models 210, the weights assigned to different features, and/or combinations of features.

Accurately training the one or more feature extraction models 210 and the one or more mindfulness detection models 212 may require a large quantity of sets of video data 222, 224 and feature extraction data 226, 224 within the training database 231. In an example, to increase the quantity of available data in the training database 231, the features extracted by the feature extraction model 210 during a new video capture may be stored for future use in the training database 231. The extracted features may concurrently or subsequently be associated (e.g., by a domain expert) with an identifier of mindful activity 230 or not mindful activity 232. For instance, the features extracted by the feature extraction model 210 may be used to train the one or more mindfulness detection models 212. In another example, video may be captured and stored as video data 222 or 224 for future use in the training database 231. The captured video may concurrently or subsequently be associated (e.g., by a domain expert) with an identifier of mindful activity 230 or not mindful activity 232. For instance, the captured video may be used to train the one or more mindfulness detection models 212. Accordingly, the one or more mindfulness detection models 212 may be continually trained as new videos are captured by the mindfulness detection system 104.

Figure 3:
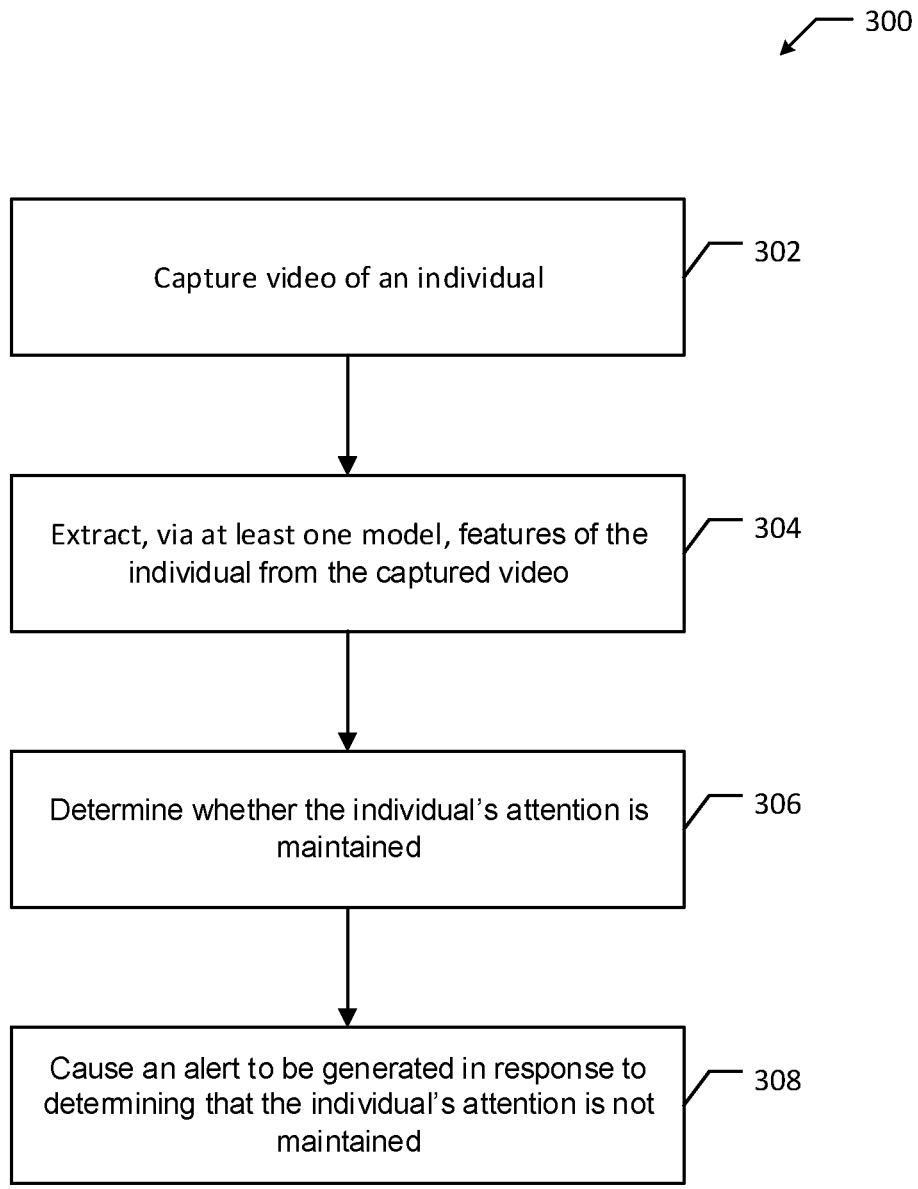
FIG. 3 illustrates a flow chart of a method for detecting whether an individual is mindful, according to an aspect of the present disclosure.

FIG. 3 illustrates a flow chart of an example method 300 for detecting whether an individual is being mindful. Although the example method 300 is described with reference to the flowchart illustrated in FIG. 3, it will be appreciated that many other methods of performing the acts associated with the method 300 may be used. For example, the order of some of the blocks may be changed, certain blocks may be combined with other blocks, and some of the blocks described are optional. The method 300 may be performed by processing logic that may comprise hardware (circuitry, dedicated logic, etc.), software, or a combination of both.

The example method 300 may begin by capturing video of an individual (block 302). For example, the camera 206 of the mindfulness detection system 104 may capture the video. In at least some aspects, the video may be captured continuously throughout the method 300. Multiple features of the individual may be extracted from the captured video via at least one model (e.g., the feature extraction model 210) (block 304). In some aspects, the individual's features may be extracted from every frame of the video. In other aspects, the individual's features may be extracted from a predetermined sequence of frames (e.g., every other frame) of the video. In some aspects, the extracted features may include multiple positions of the individual's right eye. For instance, a position of the individual's right eye within a video frame may be extracted from each frame of a set of frames (e.g., adjacent video frames) of the captured video. In some aspects, the extracted features may include multiple positions of the individual's left eye. For instance, a position of the individual's left eye within a video frame may be extracted from each frame of a set of frames (e.g., adjacent video frames) of the captured video. If the individual's eyes are moving between frames of the captured video, this may indicate that the individual is not maintaining attention.

In some aspects, the extracted features may include multiple roll angles of the individual's head. For instance, a roll angle of the individual's head may be extracted from each frame of a set of video frames (e.g., adjacent video frames) of the captured video. As used herein, a roll angle of the individual's head is an angle of tilt of the individual's head about an axis extending from a back of the patient to a front of the patient when the patient is standing. Stated differently, a roll angle of the individual's head is an angle that the individual's head is tilted to the left or right (i.e. the individual's left or right ear is brought towards the individual's left or right shoulder). If the individual's head is moving to certain degree between frames of the captured video, this may indicate that the individual is not maintaining attention.

In some aspects, the extracted features may include multiple yaw angles of the individual's head. For instance, a yaw angle of the individual's head may be extracted from each frame of a set of video frames (e.g., adjacent video frames) of the captured video. As used herein, a yaw angle of the individual's head is an angle of turn of the individual's head about an axis extending from a top of the patient's head to patient's feet when the patient is standing. Stated differently, a yaw angle of the individual's head is an angle that the individual's head is turned to the left or right. If the individual's head is moving to certain degree between frames of the captured video, this may indicate that the individual is not maintaining attention.

In some aspects, the extracted features may include a probability that the individual is smiling. In one example, the feature extraction model 210 may be applied to a frame of the captured video and the feature extraction model 210, based on the training of the feature extraction model 210, may automatically extract the probability that the individual is smiling. For instance, the feature extraction model 210 may be trained on video frames of an individual smiling and on video frames of an individual not smiling, and based on that training the feature extraction model 210 may learn features that can effectively distinguish smiling frames from non-smiling frames. In this way, the feature extraction model 210 is used to extract features rather than features being manually crafted. In another example, a position of various portions of the individual's mouth/lips may be extracted from a video frame, or set of video frames, to calculate a probability that the individual is smiling. If the individual is smiling, this may indicate that the individual is not maintaining attention.

In some aspects, the extracted features may include a probability that the individual's left eye and/or right eye is closed. In one example, the feature extraction model 210 may be applied to a frame of the captured video and the feature extraction model 210, based on the training of the feature extraction model 210, may automatically extract the probability that the individual's left eye and/or right eye is closed. For instance, the feature extraction model 210 may be trained on video frames of an individual's left eye open and right eye closed, on video frames of an individual's left eye closed and right eye open, on video frames of both an individual's left eye and right eye open, and on video frames of both an individual's left eye and right eye closed, and based on that training the feature extraction model 210 may learn features that can effectively distinguish between frames when an individual's left eye and/or right eye is open or closed. In this way, the feature extraction model 210 is used to extract features rather than features being manually crafted. In another example, a position of various portions of the individual's left and/or right eyelids may be extracted from a video frame, or set of video frames, to calculate a probability that the individual's left and/or right eye is closed. If one or more of the individual's eyes are open, this may indicate that the individual is not maintaining attention. In one particular example, the extracted features include multiple positions of the individual's right eye, multiple positions of the individual's left eye, multiple roll angles of the individual's head, multiple yaw angles of the individual's head, a probability that the individual is smiling, a probability that the individual's left is closed, and a probability that the individual's right eye is closed.

It may then be determined, via at least one model (e.g., the mindfulness detection model 212 of the mindfulness detection system 104), whether the individual's attention is maintained based on the extracted features and multiple weighting factors (block 306). In at least some aspects, determining whether the individual's attention is maintained includes calculating a right eye motion and a left eye motion. The individual's right eye motion may be calculated as a mean displacement of the positions of the individual's right eye in the set of video frames over a predetermined time period (e.g., 5, 10, 15, etc. seconds). The individual's left eye motion may be calculated as a mean displacement of the positions of the individual's left eye in the set of video frames over a predetermined time period (e.g., 5, 10, 15, etc. seconds). In at least some aspects, determining whether the individual's attention is maintained includes calculating a roll angle motion and a yaw angle motion of the individual's head. The roll angle motion of the individual's head may be calculated as a mean difference of the roll angles of the individual's head in the set of video frames over a predetermined time period (e.g., 5, 10, 15, etc. seconds). The yaw angle motion of the individual's head may be calculated as a mean difference of the yaw angles of the individual's head in the set of video frames over a predetermined time period (e.g., 5, 10, 15, etc. seconds).

In one particular example, the mindfulness detection system 104 may determine whether the individual's attention is maintained according to Equation 1 below in which θ is a predefined threshold value and w1-w7 are corresponding weighting factors for features x1-x7. In this example, feature x1 is the left eye motion, feature x2 is the right eye motion, feature x3 is the roll angle motion, feature x4 is the yaw angle motion, feature x5 is the probability of the individual smiling, feature x6 is the probability of the individual's left eye being closed, and feature x7 is the probability of the individual's right eye being closed.

$$m = \sum_{i=1}^{7} w_i x_i - \theta.$$

Equation 1.

In some aspects, the weighting factors w1-w7 may be fixed. For example, in one aspect, w1=0.25, w2=0.25, w3=0.2, w4=0.2, w5=0.15, w6=0.1, and w7=0.1. In other aspects, the weighting factors w1-w7 may be other suitable fixed values. In some aspects, the predefined threshold value θ may be fixed. For example, in one aspect, θ=5. In other aspects, the predefined threshold value θ may be other suitable fixed values. In one particular example, w1=0.25, w2=0.25, w3=0.2, w4=0.2, w5=0.15, w6=0.1, w7=0.1, and θ=5. In some aspects, the weighting factors w1-w7 and/or the threshold value θ can be computed from a data set of annotated videos, e.g., using support vector machine or logistic regression. In some aspects, the weighting factors w1-w7 and/or the threshold value θ can be fine-tuned for each individual user, based on the individual's preferences.

The threshold value θ can adjust how conservative the mindfulness detection system 104 is in determining whether an individual is in a mindful state. Stated differently, increasing or decreasing the threshold value θ can make it more or less likely that a determination is made that an individual is in a mindful state. Adjusting the threshold value θ can therefore tune whether the mindfulness detection system errs on the side of determining an individual is mindful when the individual is not, or on the side of determining that an individual is not mindful when the individual in fact is. The threshold value θ of 5 in the example above tunes the mindfulness detection system 104 to err on the side of determining that an individual is mindful when the individual is actually not. In at least some instances, tuning the mindfulness detection system in this way can be beneficial so that the mindfulness detection system does not break an individual's focus by falsely alerting a mindful individual that they are not mindful.

In some aspects, such the mindfulness detection system 104 may continuously determine whether an individual is being mindful while video is being captured. In other aspects, the mindfulness detection system 104 may periodically (e.g., every second, three seconds, etc.) determine whether an individual is being mindful while video is being captured.

If the mindfulness detection system 104 determines that the individual's attention is not maintained (e.g., not being mindful), the mindfulness detection system 104 may generate an alert (block 308). For example, the mindfulness system 104 may emit a sound, emit a light, vibrate, etc. In some aspects, the mindfulness detection system 104 may transmit a command to an external device for the external device to generate an alert. For example, an individual might wear a smartwatch, and the mindfulness detection system 104 may transmit a command that causes the smartwatch to vibrate.

Figure 4B:
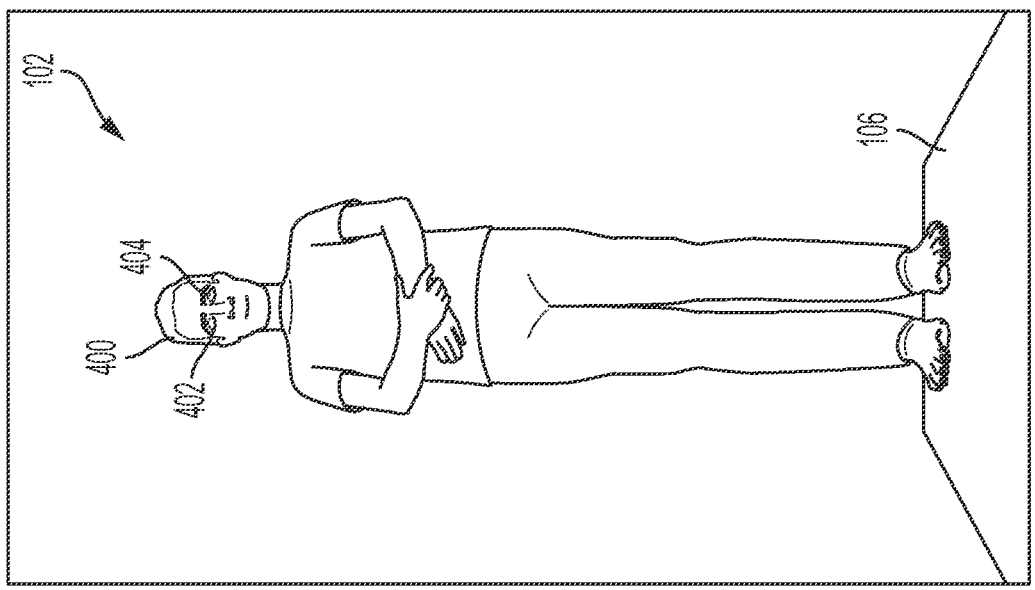
FIGS. 4A and 4B illustrate an individual in a mindful state and a not mindful state, respectively.
Figure 4A:
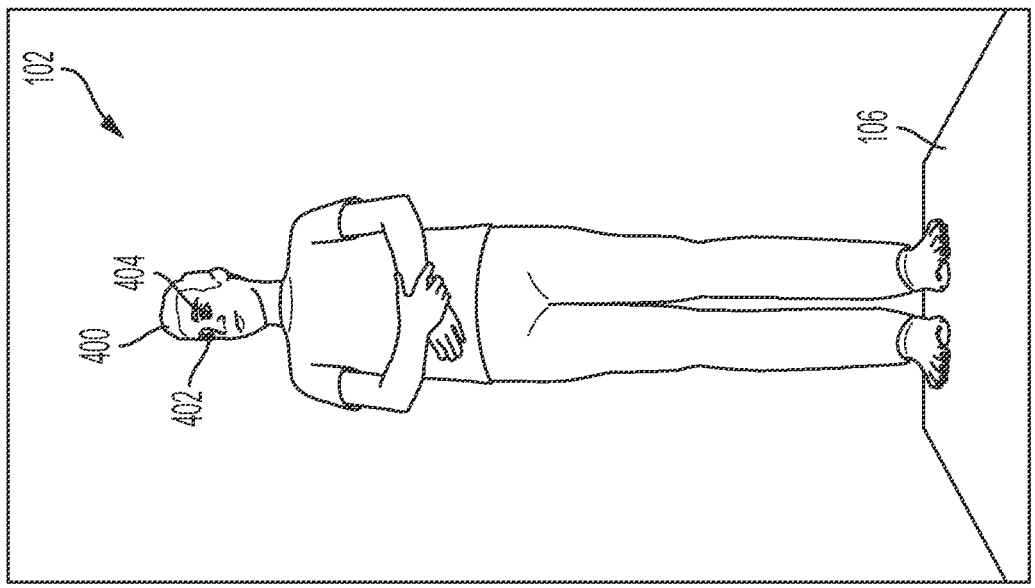

FIG. 4A illustrates an example video frame of an individual 102 that the mindfulness detection system 104 determines to be mindful (e.g., have maintained attention). The head 400 of the individual 102 is bowed with 0° of roll angle in either direction and 0° of yaw angle in either direction. Additionally, the right and left eyes 402, 404 of the individual 102 are closed. FIG. 4B illustrates an example video frame of an individual 102 that the mindfulness detection system 104 determines to not be mindful (e.g., attention is not maintained). The head 400 of the individual 102 has 0° of roll angle, but has a positive yaw angle to the right of the individual 102. Additionally, the right and left eyes 402, 404 of the individual 102 are open and the right eye 402 of the individual 102 is barely visible (e.g., there is positive right eye and left eye motion as compared to the video frame of FIG. 4A).

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A system for detecting whether an individual's attention is maintained comprising:
    a camera configured to capture video;
    a memory; and
    a processor in communication with the memory, the processor configured to:
        capture, via the camera, video of the individual,
        extract, via at least one first model, a plurality of features of the individual from the captured video, wherein the plurality of features include a plurality of positions of a left eye of the individual, a plurality of positions of a right eye of the individual, a plurality of roll angles of the individual's head, a plurality of yaw angles of the individual's head, a probability that the individual is smiling, a probability that the left eye is closed, and a probability that the right eye is closed,
        determine, via at least one second model, whether the individual's attention is maintained based on the plurality of extracted features and a plurality of weighting factors, wherein to determine whether the individual's attention is maintained based on the plurality of extracted features and the plurality of weighting factors the processor is configured to:
            calculate a left eye motion, wherein the left eye motion is a mean displacement of the plurality of positions of the left eye of the individual across a first set of frames of the captured video over a first predetermined time period;
            calculate a right eye motion, wherein the right eye motion is a mean displacement of the plurality of positions of the right eye of the individual across a second set of frames of the captured video over a second predetermined time period;
            calculate a roll angle motion, wherein the roll angle motion is a mean displacement of the plurality of roll angles of the individual's head across a third set of frames of the captured video over a third predetermined time period;
            calculate a yaw angle motion, wherein the yaw angle motion is a mean displacement of the plurality of yaw angles of the individual's head across a fourth set of frames of the captured video over a fourth predetermined time period; and
            determine whether the individual's attention is maintained based on the calculated left eye motion, right angle motion, roll angle motion, yaw angle motion, the probability that the individual is smiling, the probability that the left eye is closed, the probability that the right eye is closed, and the plurality of weighting factors, and
        cause an alert to be generated in response to determining that the individual's attention is not maintained.

2. The system of claim 1, wherein the first, second, third, and fourth set of frames are the same set of frames, and wherein the first, second, third, and fourth predetermined time periods are the same predetermined time period.

3. The system of claim 1, wherein each of the first, second, third, and fourth set of frames includes adjacent frames of the captured video.

4. The system of claim 1, wherein a weighting factor of the left eye motion is 0.25, a weighting factor of the right eye motion is 0.25, a weighting factor of the roll angle motion is 0.2, a weighting factor of the yaw angle motion is 0.2, a weighting factor of the probability of smiling is 0.15, a weighting factor of the probability that the left eye is closed is 0.1, and a weighting factor of the probability that the right eye is closed is 0.1.

5. The system of claim 1, wherein the system is a mobile computing device.

6. The system of claim 5, wherein the mobile computing device is maintained at a 45-degree angle with the ground.

7. The system of claim 1, wherein the system includes a computing device comprising the memory and the processor, and wherein the camera is separate from the computing device.

8. The system of claim 1, wherein the at least one first model is a convolutional neural network.

9. The system of claim 1, further comprising a wearable device in communication with the processor.

10. The system of claim 9, wherein the processor is configured to cause the alert to be generated on the wearable device.

11. A method for detecting whether an individual's attention is maintained comprising:
capturing, via a camera, video of the individual;
extracting, via at least one first model, a plurality of features of the individual from the captured video, wherein the plurality of features include a plurality of positions of a left eye of the individual, a plurality of positions of a right eye of the individual, a plurality of roll angles of the individual's head, a plurality of yaw angles of the individual's head, a probability that the individual is smiling, a probability that the left eye is closed, and a probability that the right eye is closed;
determining, via at least one second model, whether the individual's attention is maintained based on the plurality of extracted features and a plurality of weighting factors wherein to determine whether the individual's attention is maintained based on the plurality of extracted features and the plurality of weighting factors the processor is configured to:
calculate a left eye motion, wherein the left eye motion is a mean displacement of the plurality of positions of the left eye of the individual across a first set of frames of the captured video over a first predetermined time period;
calculate a right eye motion, wherein the right eye motion is a mean displacement of the plurality of positions of the right eye of the individual across a second set of frames of the captured video over a second predetermined time period;
calculate a roll angle motion, wherein the roll angle motion is a mean displacement of the plurality of roll angles of the individual's head across a third set of frames of the captured video over a third predetermined time period;
calculate a yaw angle motion, wherein the yaw angle motion is a mean displacement of the plurality of yaw angles of the individual's head across a fourth set of frames of the captured video over a fourth predetermined time period; and
determine whether the individual's attention is maintained based on the calculated left eye motion, right angle motion, roll angle motion, yaw angle motion, the probability that the individual is smiling, the probability that the left eye is closed, the probability that the right eye is closed, and the plurality of weighting factors; and
causing an alert to be generated in response to determining that the individual's attention is not maintained.

12. The method of claim 11, wherein determining that the individual's attention is not maintained includes determining, via the at least one model, a mindfulness score based on the plurality of extracted features and the plurality of weighting factors, and determining that the mindfulness score fails to meet a threshold.

13. The method of claim 11, wherein it is continuously determined whether the individual's attention is maintained while video of the individual is being captured via the camera.

14. The method of claim 11, wherein it is periodically determined whether the individual's attention is maintained while video of the individual is being captured via the camera.

15. The method of claim 11, wherein the plurality of features of the individual are extracted from less than every frame of the captured video.

16. The method of claim 11, wherein the roll angle of the individual's head is an angle of tilt of the individual's head about an axis extending from a back of the individual to a front of the patient when the patient is standing.

17. The method of claim 11, wherein the yaw angle of the individual's head is an angle the individual's head about an axis extending from a top of the individual's head to the individual's feet when the individual is standing.

18. A non-transitory, computer-readable medium storing instructions, which when executed by a processor, cause the processor to:
capture, via a camera, video of an individual;
extract, via at least one first model, a plurality of features of the individual from the captured video, wherein the plurality of features include a plurality of positions of a left eye of the individual, a plurality of positions of a right eye of the individual, a plurality of roll angles of the individual's head, a plurality of yaw angles of the individual's head, a probability that the individual is smiling, a probability that the left eye is closed, and a probability that the right eye is closed;
determine, via at least one second model, whether the individual's attention is maintained based on the plurality of extracted features and a plurality of weighting factors wherein to determine whether the individual's attention is maintained based on the plurality of extracted features and the plurality of weighting factors the processor is configured to:
calculate a left eye motion, wherein the left eye motion is a mean displacement of the plurality of positions of the left eye of the individual across a first set of frames of the captured video over a first predetermined time period;
calculate a right eye motion, wherein the right eye motion is a mean displacement of the plurality of positions of the right eye of the individual across a second set of frames of the captured video over a second predetermined time period;
calculate a roll angle motion, wherein the roll angle motion is a mean displacement of the plurality of roll angles of the individual's head across a third set of frames of the captured video over a third predetermined time period;
calculate a yaw angle motion, wherein the yaw angle motion is a mean displacement of the plurality of yaw angles of the individual's head across a fourth set of frames of the captured video over a fourth predetermined time period; and determine whether the individual's attention is maintained based on the calculated left eye motion, right angle motion, roll angle motion, yaw angle motion, the probability that the individual is smiling, the probability that the left eye is closed, the probability that the right eye is closed, and the plurality of weighting factors; and cause an alert to be generated in response to determining that the individual's attention is not maintained.

19. The non-transitory, computer-readable medium storing instructions of claim 18, wherein the plurality of features of the individual are extracted from every frame of the captured video.

* * * * *